US006997712B2

(12) United States Patent
Kim

(10) Patent No.: US 6,997,712 B2
(45) Date of Patent: Feb. 14, 2006

(54) TOOTH CONTAINING IMAGE THEREON

(76) Inventor: Yong Woon Kim, 5 Delea Ct., Huntington, NY (US) 11743

(*) Notice: Subject to any disclaimer, the term of this patent is extended or adjusted under 35 U.S.C. 154(b) by 59 days.

(21) Appl. No.: 10/679,584

(22) Filed: Oct. 6, 2003

(65) Prior Publication Data
US 2005/0074721 A1 Apr. 7, 2005

(51) Int. Cl.
A61C 13/08 (2006.01)
(52) U.S. Cl. .................. 433/203.1; 433/223; 264/19
(58) Field of Classification Search ............... 433/229, 433/203.1, 218, 223; 264/16, 19, 20; 29/896.1
See application file for complete search history.

(56) References Cited

U.S. PATENT DOCUMENTS

| 1,263,752 | A | * | 4/1918 | Eppstein ................. 433/203.1 |
| 4,358,321 | A | | 11/1982 | Fischer et al. ............. 106/302 |
| 4,798,536 | A | | 1/1989 | Katz ....................... 433/212.1 |
| 4,940,676 | A | | 7/1990 | Evans ........................ 501/16 |
| 5,024,790 | A | * | 6/1991 | Grossman et al. ............ 264/16 |
| 5,089,306 | A | * | 2/1992 | Grossman et al. ......... 428/35.1 |
| 5,264,398 | A | | 11/1993 | Thometzek et al. .......... 501/21 |
| 5,348,915 | A | | 9/1994 | Thometzek ................. 501/24 |
| 5,614,330 | A | | 3/1997 | Panzera et al. ............. 428/697 |
| 5,624,262 | A | * | 4/1997 | Yarovesky et al. ......... 433/223 |
| 5,633,090 | A | | 5/1997 | Rodek et al. ............... 428/428 |
| 5,653,791 | A | | 8/1997 | Panzera et al. .............. 106/35 |
| 5,665,472 | A | | 9/1997 | Tanaka et al. .............. 428/402 |
| 5,869,548 | A | | 2/1999 | Ikushima et al. ........... 523/116 |
| 5,944,884 | A | | 8/1999 | Panzera et al. ............... 106/35 |
| 6,089,870 | A | * | 7/2000 | Deroo ....................... 433/218 |
| 6,110,632 | A | | 8/2000 | Dunford et al. ............ 430/106 |
| 6,348,425 | B1 | | 2/2002 | Barattini et al. .............. 501/5 |
| 6,426,149 | B1 | | 7/2002 | Machida ..................... 428/434 |
| 6,481,353 | B1 | | 11/2002 | Geddes et al. .............. 101/491 |

FOREIGN PATENT DOCUMENTS

KR 1020010008010 A 2/2001
KR 1020010035505 A 5/2001

* cited by examiner

Primary Examiner—Todd E. Manahan
(74) Attorney, Agent, or Firm—St. Onge Steward Johnton & Reens LLC

(57) ABSTRACT

A dental construct is provided, which includes: a dental construct substrate; an image layer disposed at least partially on a surface of the dental construct substrate, the image layer comprising an image or information media composed of a colorant composition, the image layer fused at a temperature and being essentially free of lead and cadmium; and, a ceramic layer disposed at least partially over a surface of the dental construct substrate and covering at least the surface of the image layer, the ceramic layer comprising at least one or both of a ceramic material and a glaze material, the ceramic layer fused at a temperature, the ceramic layer being generally transparent and essentially free of lead and cadmium. The dental construct substrate preferably has a general configuration of at least a portion of a tooth. The first layer (image layer) comprises a ceramic material, preferably a metal oxide.

30 Claims, 4 Drawing Sheets

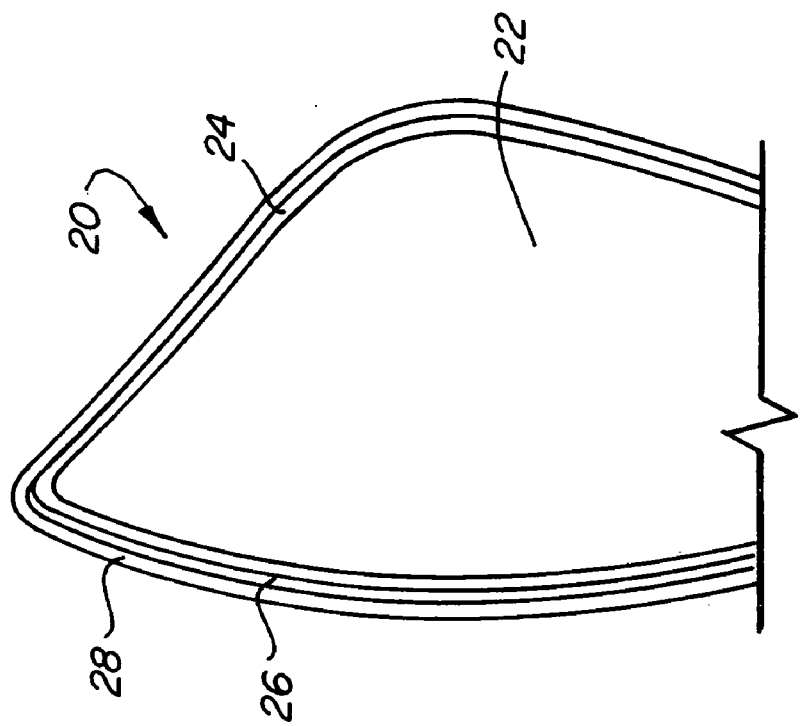
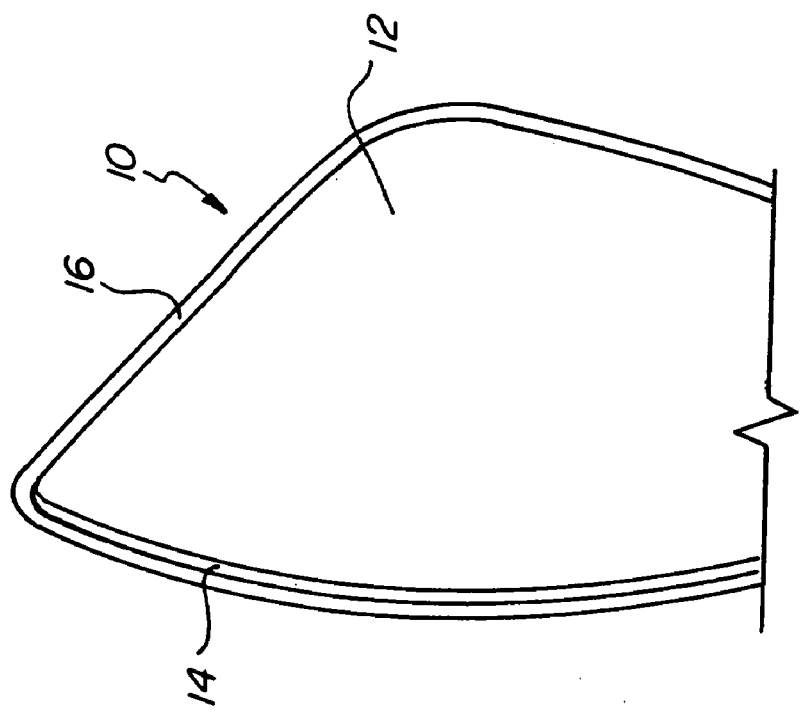

TOOTH CONTAINING IMAGE THEREON

FIELD OF THE INVENTION

The present invention relates to application of ornamental designs, images and/or informational media to the surface of natural or artificial teeth, or other dental constructs including dental crowns, veneers, inlays, onlays, false teeth, and the like.

BACKGROUND OF THE INVENTION

Long endeavors have been made in the dentistry and dental restoration area to improve the material, colors, and shapes of artificial teeth or dentin structures, particularly, for making the artificial teeth resembled to the natural teeth of a patient.

In addition, certain efforts have also been made to apply ornaments onto the surface of artificial teeth to obtain a particular fashion desired by the user. For example, in U.S. Pat. No. 6,426,149, an ornamentally designed gold or platinum foil is attached on the surface of an artificial tooth with a glaze material further coated thereon. However, use of a precious metal foil causes the cost of the ornamental application to become expensive. The cost can be greatly increased to make such ornaments to a delicate shape in light of difficulties in machining or forming of the desired shape from a sheet metal. It also limits the user's choice to several colors, for example, gold and platinum colors.

SUMMARY OF THE INVENTION

Accordingly, the present invention is directed to provide an artificial or natural tooth, or a dental construct, or similar dentistry articles containing ornaments, images, and/or information media to be noticeable from the surface of the dentistry article, that are capable of adopting a wide variety of images, figures, and the like composed of at least one or various colors. Such ornaments, images and information media are associated with at least one overcoat layer which preferably has a mechanical strength and characteristics desired by an outer layer of human or animal teeth, or similar dentistry articles, for example, resistance to physical abrasion, resistance to acid and alkali substances, a capability of matching colors and gloss/vitreosity with adjacent teeth, and freedom of toxic substances therein, such as lead and cadmium, or the like. Dental constructs referred in this application are meant to include, but without limitation thereto, restored or modified natural teeth, artificial or false teeth, dental crowns, veneers, laminates, inlays, onlays, and other dental restoration articles, and the like.

In accordance with one aspect of the present invention, a dental construct is provided, which includes: a substrate for a dental construct; and, at least one overcoat layer disposed on the surface of the substrate, the at least one layer containing a ceramic material fused with an image or information media composed of a ceramic colorant composition, the image or information media being noticeable from the surface of the dental construct, the at least one layer having a mechanical strength and characteristics suitable for the dental construct, and essentially free of lead and cadmium.

In accordance with another aspect of the present invention, a dental construct is provided, which includes: a dental construct substrate; an image layer disposed at least partially on a surface of the dental construct substrate, the image layer comprising an image or information media composed of a colorant composition, the image layer fused at a temperature and being essentially free of lead and cadmium; and, a ceramic layer disposed at least partially over a surface of the dental construct substrate and covering at least the surface of the image layer, the ceramic layer comprising at least one or both of a ceramic material and a glaze material, the ceramic layer fused at a temperature, the ceramic layer being generally transparent and essentially free of lead and cadmium.

The dental construct substrate preferably has a general configuration of at least a portion of a tooth. The first layer (image layer) comprises a ceramic material, preferably a metal oxide. The first layer preferably comprises an image consisting at least one of a figural image, a picture, an alphanumeric character, a letter, a sign, a code, data, a symbolic image, and other information for a personal or social use. The first layer is preferably disposed on a front, or rear surface of the dental construct substrate. In one preferred embodiment, when utilizing low fusing dental porcelain, the respective fusing temperature of the dental construct substrate, the image layer, and the ceramic layer is between about 1300° F. and about 1600° F. In another preferred embodiment, when utilizing high fusing dental porcelain, the respective fusing temperature of the dental construct substrate, the image layer, and the ceramic layer is between about 1600° F. and about 1900° F.

In accordance with another aspect of the present invention, a dental construct is provided, which includes: a dental construct substrate; a ceramic layer disposed at least partially on a surface of the dental construct substrate, the ceramic layer comprising a ceramic material; an image layer disposed at least partially on a surface of the ceramic layer, the image layer comprising an image or information media composed of a colorant composition, the image layer fused at a temperature and being essentially free of lead and cadmium; and, another ceramic layer disposed at least partially over a surface of the dental construct substrate and covering at least the surface of the image layer, the another ceramic layer comprising a ceramic material and fused at a temperature, the another ceramic layer being generally transparent and essentially free of lead and cadmium.

In accordance with still another aspect of the present invention, a method of producing a dental construct is provided, which comprises the steps of: providing a dental construct substrate; providing a decal sheet having an image or information media thereon; positioning the decal sheet on an appropriate surface of the dental construct substrate; firing the dental construct substrate with the decal sheet attached thereon at a temperature for a predetermined time such that the image or information media on the decal sheet is firmly fused on the surface of the dental construct substrate; applying a ceramic glaze material over the fired dental construct substrate at least on a surface covering the fused image or information media; and, firing the glaze-applied dental construct substrate at a temperature for a predetermined time such that the glaze material is fused to form a protective layer over the dental construct substrate covering at least a portion of the image or information media.

The decal sheet is preferably prepared by applying the image or information media on a blank decal sheet, for example, by printing on the blank decal sheet. The decal sheet may also be prepared by painting or drawing on the blank decal sheet.

The method may also comprises the steps of: applying a ceramic glaze material on the dental construct substrate; and, firing the glaze-applied dental construct substrate at a temperature for a predetermined time such that the glaze material is fused to form a protective layer over the dental construct substrate; wherein the above two steps are performed prior to the positioning of the image contained decal sheet on the dental construct substrate.

BRIEF DESCRIPTION OF THE DRAWINGS

The above-mentioned and other features of the present invention will now become more apparent by describing in detail several embodiments thereof with reference to the attached drawings in which:

FIG. 1 is a cross-sectional view of a dental construct (e.g., an artificial tooth) produced in accordance with one embodiment of the present invention;

FIG. 2 is a cross-sectional view of a dental construct produced in accordance with another embodiment of the present invention;

DETAILED DESCRIPTION OF THE DRAWINGS

Figure 4:
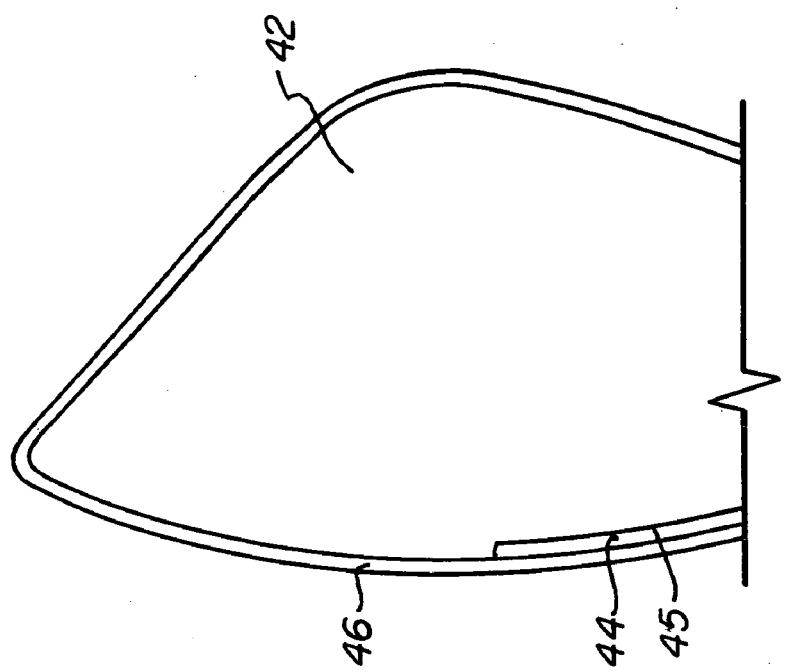
FIG. 4 is a cross-sectional view of a dental construct produced in accordance with a further embodiment of the present invention.

FIGS. 1–4 respectively show a schematic and partially sectional representation of a dental construct constructed in accordance with preferred and illustrative embodiments of the present invention. Such dental constructs may be in various forms including restored or modified natural teeth, artificial or false teeth, dental crowns, laminates, veneers, inlays, onlays, and the like. In these embodiments, such dental constructs have a respective shape of at least a portion of human or animal tooth.

Referring to FIG. 1, a dental construct 10 includes a dental construct substrate 12 generally in the form of a tooth, and a first or image layer 14 applied to at least a portion of the substrate 12. The dental construct 10 further includes a second or ceramic layer 16 coated over the first layer 12 and a substantial or the whole surface of the substrate 12. The second layer 16 may optionally be applied only a portion of the substrate 12, however, it preferably covers the whole surface of the first layer 14.

The dental construct substrate 12 may comprise or be formed from a variety of materials, such as ceramics, glass-ceramics, glass, porcelain, metal covered with porcelain, and organic or inorganic material having suitable properties for dental constructs. Such materials are known in the art, for example, some of the materials are described in U.S. Pat. No. 5,024,790, the entire disclosure of which is herein incorporated by reference. Commercially available dental porcelain or ceramic of various kinds are preferred to form the substrate particularly for artificial teeth or dental crowns. Various known formation methods can be used to make the dental construct substrate.

In one preferred embodiment, when using a low fusing porcelain material, the dental construct substrates 12 preferably has a melting temperature of between about 1300° F. and about 1600° F., more preferably between about 1400° F. and about 1500° F. In another preferred embodiment, when using a relatively high fusing porcelain material, the dental construct substrates 12 preferably has a melting temperature of between about 1600° F. and about 1900° F., more preferably between about 1700° F. and about 1800° F.

Referring still to FIG. 1, the first layer 14 is composed primarily of a colorant composition which carries an image, or other information media therein, for example, ornamental designs or pictures desired by the user who wants to bear them on their teeth for fashion or other purposes. For example, certain images such as those containing pretty flowers, national flags, or animal figures may be preferred by a certain group of people. Also, other information for a personal or social use may be contained therein, for example, information including an alphanumeric character, a letter, a sign, a code, data, a symbolic image, etc. In this embodiment, the first layer 14 is disposed over a substantial portion of the front face of the tooth-like substrate 12. By applying the first or image layer 14 on the front surface of the tooth, the user can show such images to other people. However, it can also be applied on the rear surface of the tooth, for example, see layer 30 of FIG. 3 which will be described later in connection with another embodiment of the invention.

The colorant composition used to apply the first layer 14 contains a substantial portion of a ceramic material therein. It may also contain some polymeric materials or certain addictives.

It is preferred to use a variety of metallic oxides for realizing different colors. For example, a blue colorant can contain the oxides of a cobalt, chromium, aluminum, copper, manganese, zinc, etc. A yellow colorant can contain the oxides of one or more of lead, antimony, zinc, titanium, vanadium, gold, and the like. However, lead has toxicity not suitable for use for the dental construct and thus, is avoided in this invention. A red colorant can contain the oxides of one or more of chromium, iron (two valence state), zinc, gold, cadmium, selenium, or copper. However, cadmium has toxicity not suitable for use for the dental construct and thus, is avoided in this invention. A black colorant can contain the oxides of the metals of copper, chromium, cobalt, iron (plus two valence), nickel, manganese, and the like.

As mentioned above, in accordance with one important feature of the invention, the colorant composition must be essentially free of lead, cadmium, or other toxic substances in order to be safely used for teeth or dental constructs. Thus, commercially available dental stains known for applying or matching colors of the patient's teeth are preferable for the colorant composition. Also, other type of known ceramic colorants having a non-toxic nature may be applied. For example, certain non-toxic ceramic onglaze colorants sold by Sunny Ind., Co. of Korea ("Sunny LF Series Colors") may be used because they are known as non-toxic without having lead and cadmium therein.

To apply the first or image layer 14 onto the substrate 12, various methods can be used. For example, certain methods described in U.S. Pat. No. 5,024,790 (mentioned above) and U.S. Pat. No. 6,481,353 can be used. Known methods such as a thermal transfer method, and a water-slide method, and the like can be used. As described later in detail, in certain embodiments of the invention, it can be performed by a direct attachment onto the substrate 12 of a decal with a desired image thereon, followed by firing in a furnace.

Referring still to FIG. 1, the second or ceramic layer 16 is a substantially transparent ceramic or glaze layer which is formed from a fine powder of ceramic materials. Commercially available dental glaze materials and dental glass-type (transparent or translucent) porcelain are preferred in the present invention. Such dental glaze or porcelain materials generally comprise at least some of nephefine syenite, silica, china clay, whitening agents, metal oxides, etc. Also, they may contain some addictives or binders.

Referring now FIG. 2, a dental construct 20 includes a dental construct substrate 22 generally in the form of a tooth, and a first or ceramic layer 24 applied to at least a portion of the substrate 22, a second or image layer 26 disposed at least a portion of the first layer 24, and a third or ceramic layer 28 applied over the second layer 26. This embodiment is similar to that of FIG. 1 except that the first layer 24 (i.e., ceramic layer) is first disposed on the substrate 22 before the image layer 26 (i.e., the second layer) formed thereon, thus, making three layers applied. The nature and features of the first layer (ceramic layer) 24 and the third layer (ceramic layer) 28 is similar to that of the second layer (ceramic layer) 16 of FIG. 1. Also, the nature and features of the second layer (image layer) 26 is similar to that of the first layer (image layer) 14 of FIG. 1. However, as is positioned between two layers of ceramic or glaze material, the image layer 26 can be more effectively and unitarily fused together. On the other hand, the production process is more extended and thickness of the whole layer is increased. Further detailed description of this embodiment is omitted for simplicity purposes.

Figure 3:
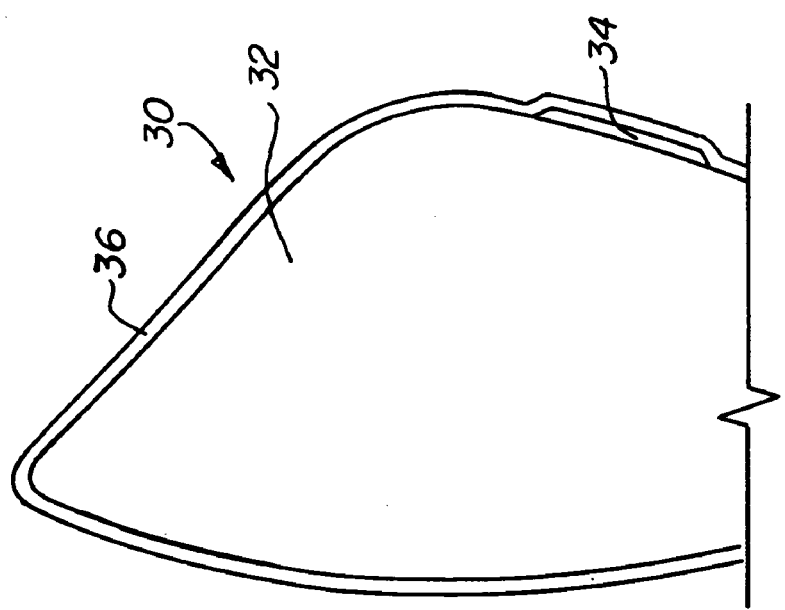
FIG. 3 is a cross-sectional view of a dental construct produced in accordance with still another embodiment of the present invention.

Referring now to FIG. 3, a dental construct 30 includes a dental construct substrate 32 generally in the form of a tooth, and a first image layer 34 applied to at a rear surface of the substrate 32, and a second ceramic layer 36 disposed over the first layer 34 and extending at least a portion of the substrate 32. This embodiment is similar to that of FIG. 1 except that the first layer 34 (i.e., image layer) is disposed on the back surface of the substrate 32. Other features of the first layer (image layer) 34 is similar to that of the first layer (image layer) 14 of FIG. 1. Also, the feature of the second layer (ceramic layer) 36 is similar to that of the second layer (ceramic layer) 16 of FIG. 1. Further detailed description of this embodiment is omitted for simplicity purposes.

By positioning the image layer on the back of the dental construct (e.g., tooth), the applied image is not noticed from the front, without changing the appearance of the user from outside. This embodiment has certain merits for record keeping purposes. For example, particular codes or numbers (such as a social security number) having importance for individual or social purposes can be safely kept, hiding at the rear side of his/her teeth. It is almost permanent and will not be erased unless the user chooses to, even burned by an ordinary fire accident. Only for illustrative example, if a solider died at a battle with a severe damage on his body while bearing his service number on the back of his teeth in accordance with the present invention, the identity of the soldier can be easily identified by checking the back side of his teeth.

Referring now to FIG. 4, a dental construct 40 includes a dental construct substrate 42 generally in the form of a tooth, and a first image layer 44 applied to at a recess 45 formed at a surface (preferably either a front or rear surface) of the substrate 42, and a second ceramic layer 46 disposed over the first layer 44 and extending at least a portion of the substrate 42. This embodiment is similar to that of FIG. 1 except that the first layer 44 (i.e., image layer) is disposed at a recess 44 formed at a surface of the substrate 42. Other features of the first layer (image layer) 44 is generally similar to that of the first layer (image layer) 14 of FIG. 1. Also, the feature of the second layer (ceramic layer) 46 is similar to that of the second layer (ceramic layer) 16 of FIG. 1. Further detailed description of this embodiment is omitted for simplicity purposes.

In this embodiment, by positioning the image layer 44 at a recess of the front or rear surface, the contour of the surface can be maintained smooth after a final layer (i.e., a ceramic layer) is applied. Also, the image layer 44 can be more securely protected because it is kept within the recess with a uniform, protective overcoat layer 46 lay thereon.

Figure 5:
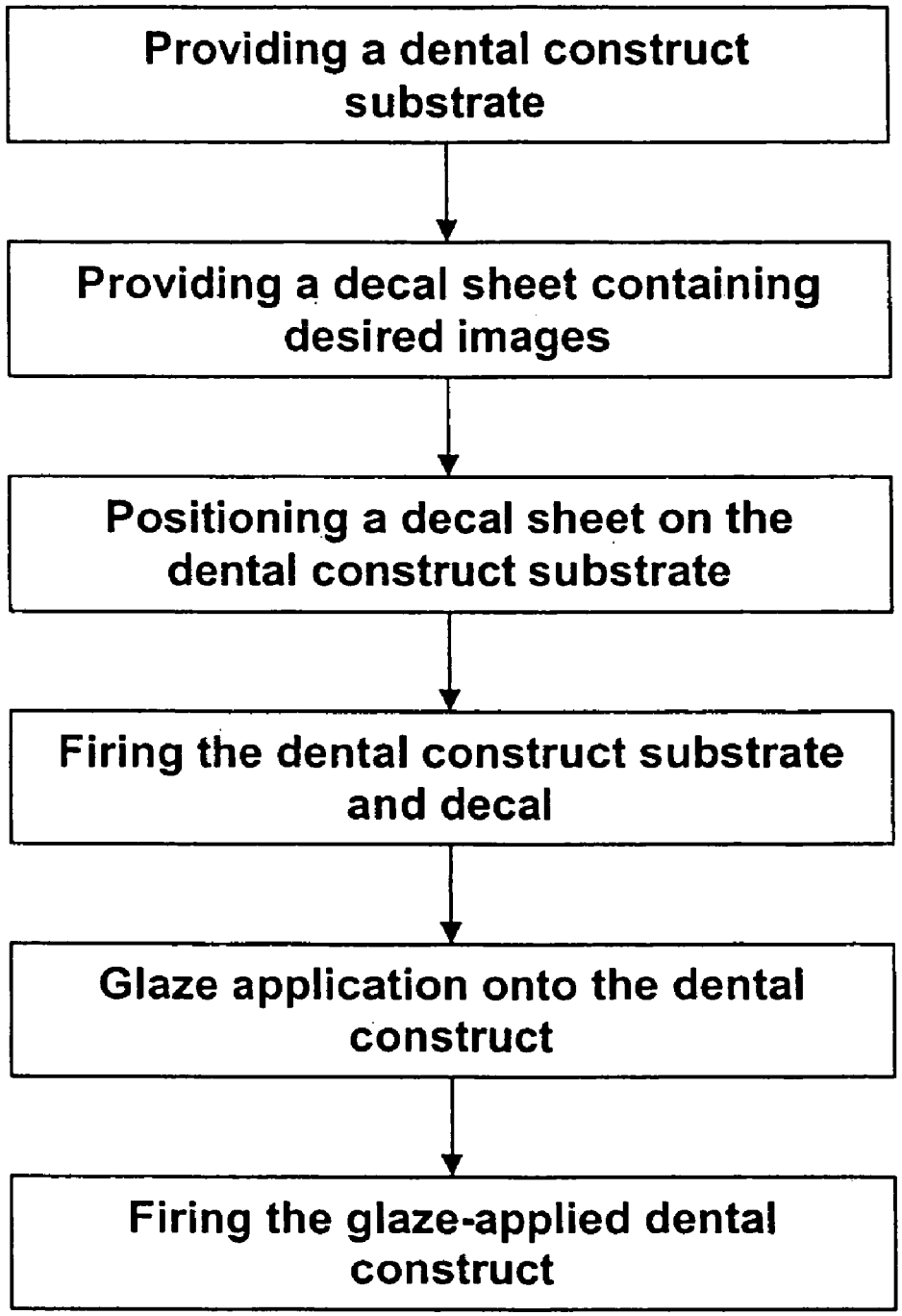
FIG. 5 is a flow chart illustrating one preferred method of making the dental construct such as that of FIG. 1.
Figure 6:
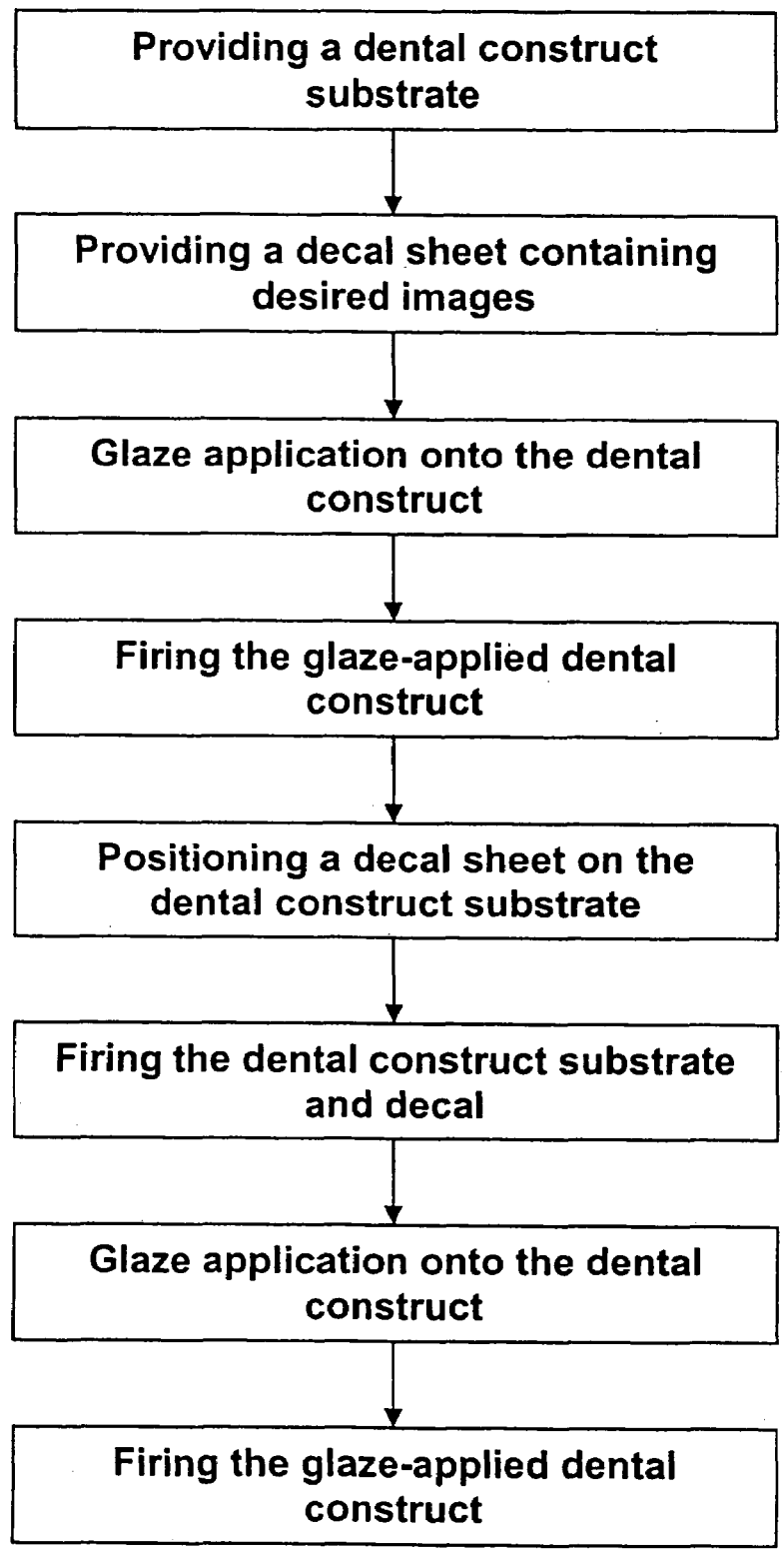
FIG. 6 is a flow chart illustrating another preferred method of making a dental construct such as that of FIG. 2.

With reference to FIGS. 5 and 6, preferred but illustrative methods of making the dental construct of the invention are described herein. Referring to FIG. 5, a dental construct substrate 12 can be formed from a variety material, such as ceramics, glass-ceramics, glass, porcelain, metal covered with porcelain and organic or inorganic material having suitable properties for dental constructs. The dental construct 12 can be formed by a variety of different known manners. One method is described herein. First, dental porcelain applicable in this invention is formed from a fine powder of "glass-like" particles. In order to fabricate a dental construct, water or some suitable liquid is added to the powder. A wet, sandy mix thus created is formed into desired shapes (e.g., a tooth shape). Then, the porcelain is fired in a furnace. The particles of porcelain are thereby fused together forming a solid construct. In this manner, porcelain may be enameled to metal or simply baked into a solid mass of pure porcelain. Restorations are typically fabricated on a replica or die of the prepared tooth. Also, additional materials may be added to the porcelain powders which improve color and strength.

In one preferred embodiment, when low fusing dental porcelain is used, the dental construct substrate 12 is selected to have a melting temperature of preferably between about 1300° F. and about 1600° F., more preferably between about 1400° F. and about 1500° F. In another preferred embodiment, when high fusing dental porcelain is used, the dental construct substrate 12 is selected to have a melting temperature of preferably between about 1600° F. and about 1900° F., more preferably between about 1700° F. and about 1800° F.

Referring still to FIG. 5, now a decal sheet having an image or information media depicted thereon is provided. One may purchase a commercially available decal sheet with a wide variety of pictures, images, and/or information composed of suitable ceramic colorant materials. However, such decal sheet and its ceramic image layer must not include toxic substances therein. Also, one may print or draw such images of information media on a decal. When drawing the images on the blank decal sheet, the colorant composition is preferably mixed with water and/or glycerin which results in a slurry-like condition, and then applied the wet composition to the decal sheet.

The decal can be formed of various materials. However, a transparent polymeric material without leaving a toxic substance upon burning is preferred.

The colorant composition used to print or draw the image layer (e.g., the first layer 14) contains a substantial portion of a ceramic material therein. It may also contain some polymeric materials or certain addictives. It is preferred to use a variety of metallic oxides for realizing different colors. For example, as described above, a blue colorant can contain the oxides of a cobalt, chromium, aluminum, copper, manganese, zinc, etc. A yellow colorant can contain the oxides of one or more of lead, antimony, zinc, titanium, vanadium, gold, and the like. A red colorant can contain the oxides of one or more of chromium, iron (two valence state), zinc, gold, cadmium, selenium, or copper. A black colorant can contain the oxides of the metals of copper, chromium, cobalt, iron (plus two valence), nickel, manganese, and the like. However, it is important to avoid such a colorant having lead and cadmium component therein because lead and cadmium have toxicity not suitable for use for the dental construct.

In one preferred embodiment, when using low fusing porcelain for the substrate 12, it is preferred to provide ceramic colorants that have a melting temperature of between about 1300° F. and about 1600° F., more preferably between about 1400° F. and about 1500° F. Thus, the ceramic colorants are selected to have a melting point similar to that of the dental construct substrate. In an alternate embodiment, when using high fusing porcelain for the substrate 12, it is preferred to provide ceramic colorants that have a melting temperature of between about 1600° F. and about 1900° F., more preferably between about 1700° F. and about 1800° F. Thus, the ceramic colorants are selected to have a melting point similar to that of the dental construct substrate. The applicant of this invention has discovered that, when the ceramic colorant layer 14 and the ceramic glaze layer 16 respectively has a melting point similar to that of the dental construct substrate, they are well adhered to the substrate upon firing, providing a longer life to the resultant constructs.

Referring still to FIG. 5, now a decal sheet with a desired image is carefully positioned on an appropriate surface of the dental construct 10. Prior to this step, if the decal sheet was prepared with a bigger size than the dental construct 10, the decal sheet should be cut into an appropriate size to fit the construct 10. Some commercial decal sheets include a backing sheet, such as a paper-like material, and then, it is preferred to place the decal sheets in water for a few minutes. Such backing sheets should be removed before or after positioning of the decal sheet.

Then, if necessary, the decal-applied dental construct substrate 12 is dried for removing moisture and air bubbles therein. Now, the resultant dental construct 10 with a decal sheet attached thereon is fired within a vacuum furnace so as to make the image or information media contained in the decal sheet fused firmly on the surface of the dental construct while burning the decal sheet out.

In one preferred embodiment, when low fusing porcelain is used for the substrate 12, the following firing conditions are preferred, however, not intending to limit thereto:
 a dry time of 5–20 min.,
 a low temperature of about 900° F.,
 starting vacuum on about 900° F.,
 heat rate of about 80° F./min.,
 vacuum level of 5–10 cm$^2$/hg (when 30 cm$^2$/hg is assumed as a maximum value),
 releasing vacuum on about 1430° F., and
 high temperature of about 1450° F.

In another preferred embodiment, when high fusing porcelain is used for the substrate 12, the following firing conditions are preferred, however, not intending to limit thereto:
 a dry time of 5–20 min.,
 a low temperature of about 1200° F.,
 starting vacuum on about 1200° F.,
 heat rate of about 80° F./min.,
 vacuum level of 5–10 cm$^2$/hg (when 30 cm$^2$/hg is assumed as a maximum value),
 releasing vacuum on about 1730° F., and
 high temperature of about 1750° F.

Firing of the dental construct substrate and the decal sheet at the furnace make the decal sheet burnt out without leaving a significant effect to the dental construct substrate 12 while the colorant image layer is fused and firmly attached onto the substrate 12. The thickness of the resulting image layer is preferably less than 0.5 mm, more preferably about 0.01 or 0.02 mm.

Referring still to FIG. 5, now a ceramic or glaze material described above (preferably in a slurry form) is applied onto the resultant substrate 12 covering at least the surface of the image layer 14. Then, it is put within a vacuum furnace and fired, for example, under a similar conditions illustrated above.

Referring now to FIG. 6, another preferred embodiment of the production method of the dental construct is described herein in connection with the dental construct 20 as described with FIG. 2. This method is substantially similar to the method discussed above in connection with FIG. 5, except that, in this method, a ceramic or glaze material application (step 150) and a glaze-applied substrate firing process (step 160) are added prior to the positioning of a decal sheet onto the substrate (step 130). See the resulting steps 210–280 in FIG. 6. Other features not mentioned here are basically similar to the formed embodiment discussed above.

While this invention has been particularly illustrated and described with reference to preferred embodiments thereof, it will be understood by those skilled in the art that various changes in form and details may be made therein without departing from the spirit and scope of the invention as defined by the appended claims.

What is claimed is:

1. A dental construct, comprising:
 a dental construct substrate;
 an image layer disposed at least partially on a surface of the dental construct substrate, the image layer comprising an image or information media composed of a colorant ceramic composition, the image layer fused with the dental construct substrate at a temperature and being essentially free of lead and cadmium; and
 a ceramic layer disposed at least partially over a surface of the dental construct substrate and covering at least the surface of the image layer, the ceramic layer comprising at least one or both of a ceramic material and a glaze material, the ceramic layer fused with the image layer at a temperature, the difference in the fusing temperature of the ceramic layer being less than 1000° F. from the fusing temperature of the image layer, the ceramic layer being generally transparent and essentially free of lead and cadmium.

2. A dental construct of claim 1, wherein the respective fusing temperature of the dental construct substrate, the image layer, and the ceramic layer is between about 1300° F. and about 1600° F.

3. A dental construct of claim 1, wherein the respective fusing temperature of the dental construct substrate, the image layer, and the ceramic layer is between about 1600° F. and about 1900° F.

4. A dental construct of claim 1, wherein the average thickness of the image layer and the ceramic layer is respectively less than 0.5 mm.

5. A dental construct of claim 1, wherein the colorant composition of the image layer comprises metal oxide pigment.

6. A dental construct of claim 1, wherein the colorant composition of the image layer is dental stain.

7. A dental construct of claim 1, wherein the dental construct substrate has a general configuration of at least a portion of a tooth.

8. A dental construct of claim 1, wherein the image layer is disposed on the surface of the dental construct substrate by utilizing a decal with the image or information media thereon.

9. A dental construct of claim 1, wherein the ceramic material or the glaze material containing in the ceramic layer is a material compatible for a dental construct or restoration of such a construct.

10. A dental construct of claim 1, wherein the ceramic layer is formed essentially from a dental glaze material.

11. A dental construct of claim 1, wherein the ceramic layer is formed essentially from dental porcelain having a transparent or translucent nature upon fusing at a temperature.

12. A dental construct of claim 1, wherein the image layer comprises an image consisting at least one of a figural image, a picture, an alphanumeric character, a letter, a sign, a code, data, a symbolic image, and other information for a personal or social use.

13. A dental construct of claim 1, wherein the image layer is disposed on a front surface of the dental construct substrate.

14. A dental construct of claim 1, wherein the image layer is disposed on a rear surface of the dental construct substrate.

15. A dental construct of claim 1, wherein the image layer is disposed on a recessed surface of the dental construct substrate.

16. A dental construct of claim 1, wherein the image layer is disposed in a recess formed on the surface of the dental construct substrate.

17. A dental construct, comprising:
a dental construct substrate;
a ceramic layer disposed at least partially on a surface of the dental construct substrate, the ceramic layer comprising a ceramic material;
an image layer disposed at least partially on a surface of the ceramic layer, the image layer comprising an image or information media composed of a colorant ceramic composition, the image layer fused with the ceramic layer at a temperature and being essentially free of lead and cadmium; and
another ceramic layer disposed at least partially over a surface of the dental construct substrate and covering at least the surface of the image layer, the another ceramic layer comprising a ceramic material and fused with the image layer at a temperature, the another ceramic layer being generally transparent and essentially free of lead and cadmium.

18. A dental construct of claim 17, wherein the respective fusing temperature of the dental construct substrate, the image layer, and each of the ceramic layers is between about 1300° F. and about 1600° F.

19. A dental construct of claim 17, wherein the respective fusing temperature of the dental construct substrate, the image layer, and each of the ceramic layers is between about 1600° F. and about 1900° F.

20. A dental construct comprising:
a substrate for a dental construct, the substrate having a front surface and a rear surface when seen from outside after installation into a mouth; and
at least one overcoat layer disposed on the rear surface of the substrate, the at least one layer containing a ceramic material fused with an image or information media composed of a ceramic colorant composition, the image or information media containing characters, codes or numbers usable for identification of a person or animal bearing the dental construct, the image or information media being noticeable from the rear surface of the dental construct without changing the appearance thereof from the front surface of the dental construct, the at least one layer having a mechanical strength and characteristics suitable for the dental construct, and essentially free of lead and cadmium.

21. A dental construct of claim 20, wherein the rear surface of the dental construct substrate includes a recess and the image or information media is disposed in the recess.

22. A method of producing a dental construct, comprising the steps of:
providing a dental construct substrate;
providing a decal sheet having an image or information media composed of a colorant ceramic composition;
positioning the decal sheet on an appropriate surface of the dental construct substrate;
firing the dental construct substrate with the decal sheet attached thereon within a vacuum furnace at a temperature for a predetermined time such that the image or information media on the decal sheet is firmly fused on the surface of the dental construct substrate;
applying a ceramic glaze material over the fired dental construct substrate at least on a surface covering the fused image or information media; and
firing the glaze-applied dental construct substrate at a temperature for a predetermined time such that the glaze material is fused to form a protective layer over the dental construct substrate covering at least a portion of the image or information media, the firing temperature of the glaze-applied dental construct being within a range of difference less than 100° F. from the firing temperature of decal-attached dental construct.

23. The method of claim 22, wherein the image contained decal sheet is provided by printing the image or information media on the blank decal sheet.

24. The method of claim 23, wherein the image contained decal sheet is provided by a screen printing method.

25. The method of claim 22, wherein the image contained decal sheet is provided by painting or drawing the image or information media on the blank decal sheet.

26. The method of claim 22 further comprising the step of cutting the imaged decal sheet to an appropriate size prior to the positioning on the dental construct substrate.

27. The method of claim 22, wherein the dental construct substrate is a dental porcelain or a dentin substrate.

28. The method of claim 22 further comprising the steps of:
applying a ceramic glaze material on the dental construct substrate; and
firing the glaze-applied dental construct substrate at a temperature for a predetermined time such that the glaze material is fused to form a protective layer over the dental construct substrate;
wherein the above two steps are performed prior to the positioning of the image contained decal sheet on the dental construct substrate, and the above specified temperature of firing the glaze-applied dental construct being within a range of difference less than 100° F. from the firing temperature of decal-attached dental construct.

29. The method of claim 22, wherein the respective fusing temperature of the dental construct substrate and the ceramic glaze material are between about 1300° F. and about 1600° F.

30. The method of claim 22, wherein the respective fusing temperature of the dental construct substrate and the ceramic glaze material are between about 1600° F. and about 1900° F.

* * * * *